US011628174B1

(12) United States Patent
Wang et al.

(10) Patent No.: US 11,628,174 B1
(45) Date of Patent: Apr. 18, 2023

(54) PHARMACEUTICAL COMPOSITIONS AND METHODS FOR TREATING INSOMNIA

(71) Applicants: Jianmin Wang, Blacksburg, VA (US); Geping Cui, Beijing (CN)

(72) Inventors: Jianmin Wang, Blacksburg, VA (US); Geping Cui, Beijing (CN)

( * ) Notice: Subject to any disclaimer, the term of this patent is extended or adjusted under 35 U.S.C. 154(b) by 0 days.

(21) Appl. No.: 17/861,070

(22) Filed: Jul. 8, 2022

(51) Int. Cl.
*A61K 31/5517* (2006.01)
*A61K 31/445* (2006.01)
*A61P 25/20* (2006.01)

(52) U.S. Cl.
CPC ........ *A61K 31/5517* (2013.01); *A61K 31/445* (2013.01); *A61P 25/20* (2018.01)

(58) Field of Classification Search
None
See application file for complete search history.

(56) References Cited

U.S. PATENT DOCUMENTS 10,898,493 B2    1/2021  Wang
2020/0323877 A1  10/2020 Wang et al.

FOREIGN PATENT DOCUMENTS

WO         2021005189 A1    1/2021

OTHER PUBLICATIONS

Hashiro et al., "A combination therapy of psychotropic drugs and antihistaminics or antiallergics in patients with chronic urticaria", Journal of Dermatological Science, vol. 11 (1996), pp. 209-213. (Year: 1996).*

Sastre, "Ebastine in the Treatment of Allergic Rhinitis and Urticaria: 30 Years of Clinical Studies and Real-World Experience", Journal of Investigational Allergology & Clinical Immunology, vol. 30(3), 2020, pp. 156-168. (Year: 2020).*
Duenas-Laita et al., "Successful treatment of chronic drug-resistant urticaria with alprazolam", Journal of Allergy and Clinical Immunology, vol. 123 (2), 2009, pp. 504-505 (Year: 2009).*
Remington, "Tablet Ingredients", Remington: The Science and Practice of Pharmacy, 21st Edition, Beringer et al. Editors, 2005, pp. 891-894. (Year: 2005).*
Balp et al., "The Impact of Chronic Urticaria from the Patient's Perspective: A Survey in Five European Countries", Patient, vol. 8, pp. 551-558, published online Oct. 17, 2015) (Year: 2015).*
SingleCare, "Xanax dosage, forms, and strengths", downloaded on Nov. 4, 2022 from "www.singlecare.com/prescription/xanax/dosage", Jul. 13, 2021. (Year: 2021).*
Pharma Guide, "Kestine (ebastine) 20 mg, 10 mg, 5 mg Tablets & Syrup", downloaded on Nov. 4, 2022 from "pharmaguide.org/kestine.html", 2013. (Year: 2013).*
P. Van Cauwenberge, T. De Beider & Lien Sys, "A review of the second-generation antihistamine eszopiclone ebastine for the treatment of allergic disorders". Expert Opinion on Pharmacotherapy, 2004; 5:8, 1807-1813.
Sastre, "Ebastine in allergic rhinitis and chronic idiopathic urticaria". Current Topics in Med. Chem. 2011, 11: 221-240.
L. Wiserman and D. Faulds, "Ebastine, A Review of its Pharmacological Properties and Clinical Efficacy in the Treatment of Allergic Disorders". Drugs 1996, 51(2): 260-277.
A. Kales, E O Bixler, et al., "Alprazolam: effects on sleep and withdrawal phenomena" J Clin Pharmacol . 1987, 27(7): 508-15.
ISR/WO for PCT/US2022/036579 dated Oct. 17, 2022.
Montoro et al. J. Investig. Allergology and Clinical Immunology. vol. 23, Suppl. 1, pp. 17-26.

* cited by examiner

*Primary Examiner* — Savitha M Rao
*Assistant Examiner* — Gregg Polansky
(74) *Attorney, Agent, or Firm* — Rhodes IP PLC; Christopher R. Rhodes

(57) ABSTRACT

Pharmaceutical compositions comprising ebastine and alprazolam are disclosed. Methods of using the pharmaceutical compositions for treating patients suffering from insomnia are also disclosed.

12 Claims, 1 Drawing Sheet

PHARMACEUTICAL COMPOSITIONS AND METHODS FOR TREATING INSOMNIA

FIELD OF THE INVENTION

The invention relates to the field of practical medicine, namely, to the use of pharmaceutical compositions for treating, preventing, and/or alleviating manifestations of insomnia or symptoms thereof.

SUMMARY OF THE INVENTION

Insomnia is often diagnosed through the presence of polysomnographic evidence of disturbed sleep, such as a long sleep latency, frequent nocturnal awakenings, or prolonged periods of wakefulness during the sleep period or even frequent transient arousals. Various population-based studies show that approximately 30-40% of a variety of adult samples drawn from different countries report one or more of the symptoms of insomnia: difficulty initiating sleep, difficulty maintaining sleep, waking up too early, and in some cases, nonrestorative or poor quality of sleep. Particularly, insomnia has a very negative impact on vulnerable patient groups, including active military personnel and veterans, patients with coexisting psychiatric and medical disorders, those in life transitions such as menopause, and elderly persons. Due to its chronicity, insomnia is associated with substantial impairments in an individual's quality of life such as a high rate of psychiatric comorbidities. Insomnia even poses a greater health risk due to the increased occurrence of daytime accidents.

Treatments for insomnia include benzodiazepine receptor agonists, such as triazolam, estazolam, zolpidem, zaleplon, eszopiclone, etc.; melatonin agonists, such as ramelteon; tricyclic antidepressants, such as doxepin; orexin receptor antagonists, such as suvorexant. These drugs do carry risks of tolerance, dependence, memory impairment, depression, headache, dizziness, somnolence, and so on.

Clinically, new treatments for insomnia are urgently needed that have significantly fewer side effects and can be provided to a wider range of patients experiencing insomnia who have additional medical or mental conditions.

Inflammation can be defined as one of the immune responses for protecting living organisms from damage. The immune system can be triggered by various factors such as pathogens, damage to cells, and stress that may induce acute or chronic inflammatory responses in organs including the brain, potentially leading to tissue damage or disease. The latest advancements in neurobiological research provide increasing evidence that inflammatory and neurodegenerative pathways play a relevant role in insomnia. Preclinical and clinical studies on insomnia highlighted an increased production of inflammatory markers, such as interleukin (IL)-1, IL-6, tumor necrosis factor (TNF)-αand interferon (INF)-αand γ, and overactivated inflammatory signaling pathways including nuclear factor kappa B (NF-κB). More recent studies have shown that blocking the biological actions of the cytokines IL-1 and TNF resulted in a reduction of physiological NREM sleep amount or NREM sleep rebound after sleep deprivation. On the other hand, increasing the availability of those cytokines promoted NREM sleep amount and intensity and suppressed REM sleep amount. These findings established both cytokines, IL-1 and TNF, as substances involved in the homeostatic regulation of sleep. Other cytokines, including IFN, IL-2, IL-4, IL-6, IL-10, IL-13, IL-15, and IL-18 also appear to have some sleep regulatory properties. The anti-inflammatory cytokines IL-4, IL-10, and IL-13 have been reported to attenuate NREM sleep amount in rabbits, while the pro-inflammatory acting cytokines IFN-γ, IL-2, IL-6, IL-15, and IL-18 have NREM sleep-promoting actions in animal models.

Ebastine is a second-generation H1-receptor antagonist and administered orally once-daily and is indicated for the treatment of the symptoms of allergic rhinitis and chronic idiopathic urticaria. In addition to blocking the H1-receptor, ebastine has other effects that contribute to its antiallergy effects. In vitro and in vivo studies, as well as clinical trials, the effects of ebastine on various mediators of inflammation have been shown. Ebastine significantly inhibits the anti-IgE-induced release of prostaglandin D2 (PGD2) and leukotrienes C4/D4 (LTC4/D4). Ebastine also inhibited the release of cytokines, including granulocyte-macrophage colony-stimulating factor (GM-CSF), tumour necrosis factor-a and interleukin-8. Its metabolite, carebastine, inhibits the release of PGD2.

Alprazolam is one of the most widely prescribed benzodiazepines for the treatment of generalized anxiety disorder and panic disorder. The neurochemical mechanism for alprazolam's anxiolytic effects are not fully understood but research shows that benzodiazepines enhance central nervous system GABAergic pre- and postsynaptic inhibition. Also, alprazolam binds both GABA and benzodiazepine receptors, each of which has both GABA and benzodiazepine recognition sites and GABA and related agents enhance the specific binding of benzodiazepine. Alprazolam may thus exert therapeutic anxiolytic effects via interaction with a high-affinity binding site on brain receptors. These benzodiazepine receptors interact with GABA receptors, potentiating GABAs synaptic inhibitory effect. We hypothesize that alprazolam's effects of nervous system GABAergic pre- and postsynaptic inhibition through GABA and benzodiazepine receptors stabilize the anti-inflammatory cytokines IL-4, IL-10, and IL-13. Alprazolam's antidepressant effects rest on its effect on $^3$H-DHA binding, indicating an ability to decrease beta adrenergic receptor sensitivity, specifically when given chronically at higher doses. Studies have shown that alprazolam significantly decreases the length of REM periods and frequency of REM burst activities as well as increases REM latency. We believe a differential effect of alprazolam versus other benzodiazepines on REM latency is of potential clinical importance.

Therefore, a unique combination of ebastine with alprazolam would potentially be, in terms of working through multi-mechanisms of actions, effective in the treatment of insomnia.

The present invention includes a pharmaceutical composition that comprises two active pharmaceutical ingredients. This pharmaceutical composition comprises the first active ingredient that is ebastine and the second active ingredient that is alprazolam. If desired, the composition can include only ebastine and alprazolam as pharmaceutically active ingredients, e.g., the composition can consist of only ebastine and alprazolam as pharmaceutically active ingredients. Pharmaceutically inactive materials such as excipients may also be present in the pharmaceutical composition.

In some embodiments of this invention, ebastine in the pharmaceutical composition is provided in an amount of about 5 mg to about 50 mg and alprazolam in an amount of about 0.2 mg to about 2 mg.

The present invention also includes an oral pharmaceutical dosage form of the pharmaceutical composition that is a solid, liquid, or gel form. The oral pharmaceutical dosage form can include only ebastine and alprazolam as pharmaceutically active ingredients. For example, the oral pharmaceutical dosage form can consist of only ebastine and alprazolam as pharmaceutically active ingredients, e.g., only ebastine and alprazolam optionally in combination with non-pharmaceutically active materials such as excipients, binders, etc.

The present invention further includes use of the composition, such as by oral dosage, through administration to patients with insomnia.

In some embodiments of this invention, an oral pharmaceutical dosage form of the pharmaceutical composition containing ebastine in an amount of about 5 mg to about 50 mg and alprazolam in an amount of about 0.2 mg to about 2 mg is administered to patients with insomnia.

Embodiments include Aspect 1, which are pharmaceutical compositions comprising: ebastine; alprazolam; and one or more pharmaceutically acceptable excipients.

Aspect 2 is the pharmaceutical composition of Aspect 1, wherein the ebastine is present in the pharmaceutical composition in an amount in the range of about 5 mg to about 50 mg.

Aspect 3 is the pharmaceutical composition of Aspect 1 or 2, wherein the alprazolam is present in the pharmaceutical composition in an amount in the range of about 0.2 mg to about 2 mg.

Aspect 4 is the pharmaceutical composition of any of Aspects 1-3, wherein the ebastine is present in the pharmaceutical composition in an amount in the range of about 5 mg to about 25 mg.

Aspect 5 is the pharmaceutical composition of any of Aspects 1-4, wherein the alprazolam is present in the pharmaceutical composition in an amount in the range of about 0.4 mg to about 2.0 mg.

Aspect 6 is the pharmaceutical composition of any of Aspects 1-5, wherein: the ebastine is present in the pharmaceutical composition in an amount in the range of about 5 mg to about 50 mg; and the alprazolam is present in the pharmaceutical composition in an amount in the range of about 0.2 mg to about 2 mg.

Aspect 7 is the pharmaceutical composition of any of Aspects 1-6, wherein: the ebastine is present in the pharmaceutical composition in an amount in the range of about 5 mg to about 25 mg; and the alprazolam is present in the pharmaceutical composition in an amount in the range of about 0.2 mg to about 2.0 mg.

Aspect 8 is the pharmaceutical composition of any of Aspects 1-7, wherein the pharmaceutical composition is formulated as an oral pharmaceutical dosage form.

Aspect 9 is the pharmaceutical composition of any of Aspects 8, wherein the oral pharmaceutical dosage form is a solid form or a liquid form or a gel form.

Aspect 10 is a method comprising: administering a pharmaceutical composition to a patient; wherein the pharmaceutical composition comprises effective amounts of ebastine and alprazolam; and wherein the effective amounts together are sufficient to treat insomnia of the patient.

Aspect 11 is the method of Aspect 10, wherein the pharmaceutical composition is administered once or twice a day, or once every 2 or 3 or 4 days to the patient in an oral solid or liquid form or a gel form.

Aspect 12 is the method of any of Aspects 10-11, wherein the ebastine is present in the pharmaceutical composition in an amount in the range of about 5 mg to about 50 mg.

Aspect 13 is the method of any of Aspects 10-12, wherein the alprazolam is present in the pharmaceutical composition in an amount in the range of about 0.2 mg to about 2.0 mg.

Aspect 14 is the method of any of Aspects 10-13, wherein the ebastine is present in the pharmaceutical composition in an amount in the range of about 5 mg to about 25 mg.

Aspect 15 is the method of any of Aspects 10-14, wherein the alprazolam is present in the pharmaceutical composition in an amount in the range of about 0.2 mg to about 2.0 mg.

Aspect 16 is the method of any of Aspects 10-15, wherein: the ebastine is present in the pharmaceutical composition in an amount in the range of about 5 mg to about 50 mg; and the alprazolam is present in the pharmaceutical composition in an amount in the range of about 0.2 mg to about 2.0 mg.

Aspect 17 is the method of any of Aspects 10-16, wherein: the ebastine is present in the pharmaceutical composition in an amount in the range of about 5 mg to about 25 mg; and the alprazolam is present in the pharmaceutical composition in an amount in the range of about 0.2 mg to about 2.0 mg.

DETAILED DESCRIPTION OF THE INVENTION

Through clinical practices, the inventors of the present invention found that a pharmaceutical composition with oral dosage forms comprising the active agents, ebastine and alprazolam, is suitable for treating patients, e.g., humans, suffering from insomnia and/or symptoms thereof, such as difficulty falling asleep, waking up during the night, waking up too early, daytime tiredness/sleepiness, etc.

The detailed description provided below is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

Definitions

As used in the present specification, the following words and phrases are generally intended to have the meanings as set forth below, except to the extent that the context in which they are used indicates otherwise.

Figure 1:
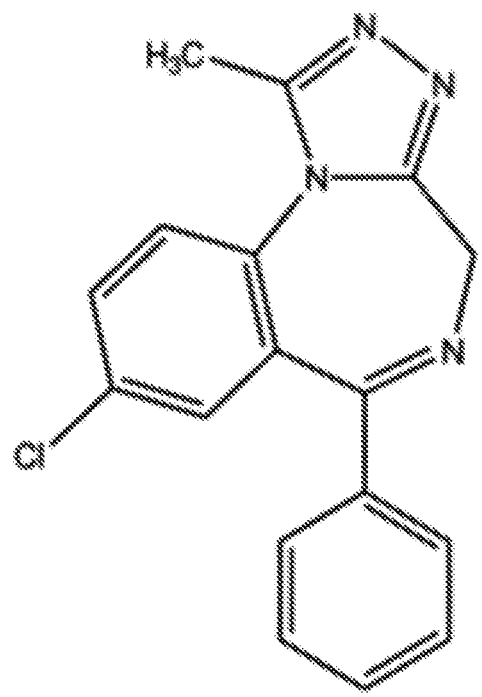
FIG. 1 shows a chemical structure of alprazolam.

As used herein, the term "alprazolam" refers to 8-chloro-1-methyl-6-phenyl-4H-s-triazolo[4,3-a] [1,4]benzodiazepine as shown in FIG. 1.

Figure 2:
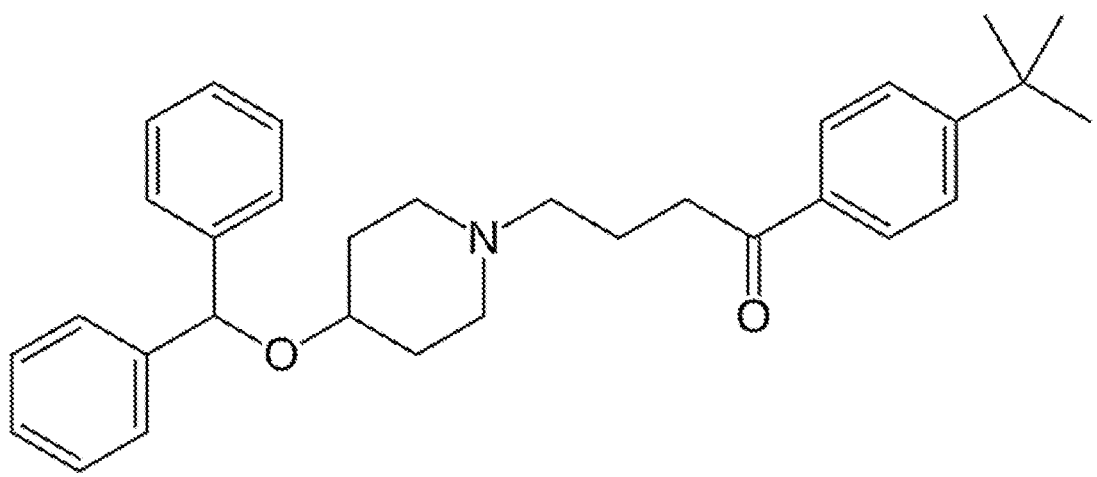
FIG. 2 shows a chemical structure of ebastine.

As used herein, the term "ebastine" refers to 4-diphenylmethoxy-1-[3-(4-tert-butylbenzoyl)-propyl] piperidine as shown in FIG. 2.

As used herein, "treating" or "treatment" means complete cure or incomplete cure, or it means that the symptoms of the underlying disease or associated conditions are at least reduced and/or delayed, and/or that one or more of the underlying cellular, physiological, or biochemical causes or mechanisms causing the symptoms are reduced, delayed and/or eliminated. It is understood that reduced or delayed, as used in this context, means relative to the state of the untreated disease, including the molecular state of the untreated disease, not just the physiological state of the untreated disease.

The term "effective amount" refers to an amount that is sufficient to affect treatment, as defined below, when administered to a mammal in need of such treatment. The therapeutically effective amount will vary depending upon the patient being treated, the weight and age of the patient, the severity of the disease condition, the manner of administration and the like, which can readily be determined by one of ordinary skill in the art. The pharmaceutical compositions may be administered in either single or multiple doses by oral administration. Administration may be by way of any one or more of capsule, tablet, gel, spray, drops, solution, suspensions, syrups, or the like.

The term "about" used herein in the context of quantitative measurements means the indicated amount ±10%. For example, with a ±10% range, "about 2 mg" can mean 1.8-2.2 mg.

The pharmaceutical compositions may be formulated for pharmaceutical use using methods known in the art, for example, Ansel's Pharmaceutical Dosage Forms and Drug Delivery Systems Tenth (by Loyd Allen, 2013) and Handbook of Pharmaceutical Manufacturing Formulations (Volumes 1-6 by Sarfaraz K. Niazi). Accordingly, incorporation of the active compounds and a controlled, or slow release matrix may be implemented.

Either fluid or solid unit dosage forms can be readily prepared for oral administration, for example, admixed with any one or more of conventional ingredients such as dicalcium phosphate, magnesium aluminum silicate, magnesium stearate, calcium sulfate, starch, talc, lactose, acacia, methyl cellulose and functionally similar materials as pharmaceutical excipients or carriers. A sustained release formulation may optionally be used. In older or incoherent subjects sustained release formulations may even be preferred. Capsules may be formulated by mixing the pharmaceutical composition with a pharmaceutical diluent which is inert and inserting this mixture into a hard gelatin capsule having the appropriate size. If soft capsules are desired, a slurry of the pharmaceutical composition with an acceptable vegetable, light petroleum or other inert oil can be encapsulated by forming into a gelatin capsule.

Suspensions, syrups and elixirs may be used for oral administration or fluid unit dosage forms. A fluid preparation including oil may be used for oil soluble forms. A vegetable oil such as corn oil, peanut oil or a flower oil, for example, together with flavoring agents, sweeteners and any preservatives produces an acceptable fluid preparation. A surfactant may be added to water to form a syrup for fluid unit dosages. Hydro-alcoholic pharmaceutical preparations may be used having an acceptable sweetener, such as sugar, saccharin or other non-nutritive sweetener, and/or a biological sweetener and/or a flavoring agent, such as in the form of an elixir.

The solid oral dosage formulation of this disclosure means a form of tablets, caplets, bi-layer tablets, film-coated tablets, pills, capsules, or the like. Tablets in accordance with this disclosure can be prepared by any mixing and tableting techniques that are well known in the pharmaceutical formulation industry. In some examples, the dosage formulation is fabricated by direct compressing the respectively prepared sustained-release portion and the immediate-release portion by punches and dies fitted to a rotary tableting press, ejection or compression molding or granulation followed by compression.

The pharmaceutical compositions provided in accordance with the present disclosure can be typically administered orally. This disclosure therefore provides pharmaceutical compositions that comprise a solid dispersion comprising ebastine and alprazolam as described herein and one or more pharmaceutically acceptable excipients or carriers including but not limited to, inert solid diluents and fillers, diluents, including sterile aqueous solution and various organic solvents, permeation enhancers, solubilizers, disintegrants, lubricants, binders, glidants, adjuvants, and combinations thereof. Such compositions are prepared in a manner well known in the pharmaceutical arts (see, e.g., Ansel's Pharmaceutical Dosage Forms and Drug Delivery Systems, Tenth (by Loyd Allen, 2013) and Handbook of Pharmaceutical Manufacturing Formulations (Volumes 1-6 by Sarfaraz K. Niazi)).

The pharmaceutical compositions may further comprise pharmaceutical excipients such as diluents, binders, fillers, glidants, disintegrants, lubricants, solubilizers, and combinations thereof. Some examples of suitable excipients are described herein. When the pharmaceutical compositions are formulated into tablets, tablets may be uncoated or may be coated by known techniques including microencapsulation to delay disintegration and absorption in the gastrointestinal tract and thereby provide a sustained action over a longer period. For example, a time delay material such as glyceryl monostearate or glyceryl distearate alone or with a wax may be employed. In embodiments, the pharmaceutical compositions are formulated as tablets, caplets, pills, or capsules for gastrointestinal absorption, such as formulated to be capable of delaying disintegration until the pharmaceutical composition is in the gastrointestinal tract of a patient. In embodiments, delaying disintegration is achieved using a coating.

In embodiments, the pharmaceutical compositions can comprise synergistically effective amounts of ebastine and alprazolam, such as a) about 5 mg to 10 mg of ebastine and b) about 0.2 mg to 0.4 mg of alprazolam or a) about 10 mg to 20 mg of ebastine and b) about 0.4 mg to 1.2 mg of alprazolam or a) about 5 mg to 50 mg of ebastine and b) about 0.4 mg to 2.0 mg of alprazolam, or any amount of ebastine or alprazolam within these ranges. In embodiments, the alprazolam is present in the pharmaceutical composition in a synergistically effective amount relative to the amount of ebastine and can include pharmaceutical compositions comprising a) about up to and including any of 5 mg, 10 mg, 20 mg, 30 mg, 50 mg, or any amount within any of these ranges and b) about up to and including any of between 0.4 mg, 0.8 mg, 1.2 mg, 1.6 mg, 2 mg alprazolam, or any amount within any of these ranges. For example, the compositions comprising synergistically effective amounts of ebastine and alprazolam can comprise a) about 5 mg of ebastine and b) about 0.4 mg of alprazolam. Further, for example, compositions of the invention can comprise ebastine present in an amount in the range of about 5 mg to about 50 mg and a synergistically effective amount of alprazolam in an amount in the range of about 0.4 mg to about 2 mg. In embodiments, the synergistically effective amounts can be such that the amount of ebastine present in the composition can be equal to, more than, or less than the amount of alprazolam present in the composition. In embodiments, the synergistically effective amounts are such that the ebastine is present in the pharmaceutical composition in an amount of at least 5 mg and alprazolam is present in an amount of at least 0.4 mg. In embodiments, the synergistically effective amounts can be such that the amount of ebastine present in the composition can be the same as, or 2 times as much, or 3 times as much, or 4, 5, 6, 7, 8, 9, 10, 15, 20, 25, 30, 35, 10, 15, or 50 times as much as the amount of alprazolam present in the composition, or vice versa. Any one or more of the compositions of the invention can be used with any one or more the methods of the invention disclosed herein, or other methods of using the compositions.

It will be understood, that the amount of the pharmaceutical composition containing ebastine and alprazolam actually administered usually will be determined by a physician, in the light of the relevant circumstances, including the condition to be treated, the chosen route of administration, the actual compound administered and its relative activity, the age, weight and response of the individual patient, the severity of the patient's symptoms, and the like.

The pharmaceutical compositions, pharmaceutical dosage forms, and tablets containing ebastine and alprazolam as described herein are administered to a patient suffering from insomnia, by administration (such as oral administration) once daily, twice daily, up to four times a day, once every other day, once a week, two times a week, three times a week, four times a week, or five times a week, or combinations thereof.

In embodiments, patients are administered the pharmaceutical composition(s) with a therapeutic effective daily dosage of ebastine in the range of about 5 mg to about 50 mg and alprazolam in an amount in the range of about 0.2 mg to about 2 mg.

In embodiments, the pharmaceutical dosage forms and tablets of pharmaceutical compositions containing ebastine, such as ebastine and alprazolam as described herein are effective in reversing, reducing, alleviating, and/or treating insomnia in about 1-8 weeks, such as within 1, 2, 3, 4, 5, 6, 7, or 8 weeks, or any range in between.

The following Examples are illustrative and should not be interpreted to limit the scope of the claimed subject matter.

Example 1

A 58-year-old male patient had been treated with ebastine (20 mg once a day) for his persistent insomnia (difficulty of falling to asleep) along with severe allergic rhinitis for about 3 months but his insomnia had no improvement and allergic rhinitis only improved marginally. Then he was treated with the combination of ebastine (10 mg) and alprazolam (0.4 mg) once daily. After the $5^{th}$ day of treatment, his insomnia was improved by 50%; after 14 days of treatment he had no symptoms of insomnia and allergic rhinitis. He was on this combination treatment for 3 months and never had any symptoms of insomnia and severe allergic rhinitis.

Example 2

A 48-year-old male patient had been treated with alprazolam (0.8 mg, twice daily) for his chronic insomnia along with depression for 2 months and he experienced no improvement. Then he was switched to the treatment of the combination of ebastine (10 mg) and alprazolam (0.4 mg) twice daily and the treatment lasted for 30 days. After 14 days of his initial treatment with the combination, he had no insomnia and depression was improved by 80%. At the end of 30 day treatment, the patient was experiencing around 7-hour sleep time daily and had no any depression symptoms.

Example 3

A 55-year-old male patient had insomnia for more than 2 months before he was provided with medications. He had been treated with zolpidem (10 mg daily for 1 month) and then eszopiclone (1 mg daily for 2 weeks) but could not tolerate the side effects of headache and dizziness associated with those drugs. After that, he was treated with the combination of azelastine (2 mg) and alprazolam (0.4 mg) daily for 1 week but this combination was not effective to eliminate his insomnia. Then he was switched to the combination of ebastine (20 mg) and alprazolam (0.8 mg) daily for 1 week and his sleep latency decreased by 40% and sleep duration improved by 50% and had no complains of severe side effects. Starting from the 5th week of the treatment with this new combination, he started experiencing no insomnia. The combination of ebastine and alprazolam is effective for treatment of insomnia without intolerable side effects.

Example 4

A 43-year-old female patient had insomnia for more than 3 months. She was treated with eszopiclone (1 mg daily) for one week but had to withdraw from the treatment because she could not tolerate its adverse reaction of headache. After that, she was treated with the combination of ebastine (10 mg) and alprazolam (0.4 mg) daily. After 5 weeks of the treatment, she had no insomnia and the adverse drug reaction was well tolerated during the 5 weeks of treatment.

REFERENCES

P. Van Cauwenberge, T. De Belder & Lien Sys, "A review of the second-generation antihistamine eszopiclone ebastine for the treatment of allergic disorders". Expert Opinion on Pharmacotherapy, 2004; 5:8, 1807-1813.

J. D. Lie, K. N. Tu, D. D. Shen and B. M. Wong, "Pharmacological Treatment of Insomnia". P&T, 2015, Vol 40, No. 11 759-771.

T. Roth, T. Roehrs, and R. Pies "Insomnia: pathophysiology and implication for treatment". Sleep Med Rev, 2007; 11, 71-79.

A. Qaseem, D. Kansagara, et al. "Management of Chronic Insomnia Disorder in Adults: A Clinical Practice Guideline From the American College of Physicians". Allergy 2008 63(Suppl. 89):1-20.

J. Sastre, "Ebastine in allergic rhinitis and chronic idiopathic urticaria". Current Topics in Med. Chem. 2011, 11: 221-240.

L. Wiserman and D. Faulds, "Ebastine, A Review of its Pharmacological Properties and Clinical Efficacy in the Treatment of Allergic Disorders". Drugs 1996, 51(2): 260-277.

Monica de la Pella Bravo, L. D. Serpero, et al, "Inflammatory proteins in patients with obstructive sleep apnea with and without daytime sleepiness". Sleep Breath, 2007 Sep; 11(3):177-85.

R. Nadeem, J. Molnar, et al., "Serum inflammatory markers in obstructive sleep apnea: a meta-analysis", Journal of Clinic Sleep Med (2013) Oct 15; 9(10):1003-12.

J. Gaines, A. N. Vgontzas, et al, "Inflammation mediates the association between visceral adiposity and obstructive sleep apnea in adolescents" Am J. Physiol. Endocrinol Metab., 2016 Nov 1; 311(5).

A Kales, E O Bixler, et al., "Alprazolam: effects on sleep and withdrawal phenomena" J Clin Pharmacol. 1987, 27(7): 508-15.

A. Kales, C R. Soldatos, et al.," Diazepam: effects on sleep and withdrawal phenomena" J Clin Psychopharmacol. 1988, 8(5): 340-6.

E. B. Mohns, "Discontinuation and withdrawal problems of alprazolam" West J Med. 1989,151(3): 312.

Loyd Allen, Ansel's Pharmaceutical Dosage Forms and Drug Delivery Systems, Tenth (2013).

Sarfaraz K. Niazi, Handbook of Pharmaceutical Manufacturing Formulations Volumes 1-6.

The present invention has been described with reference to particular embodiments having various features. In light of the disclosure provided above, it will be apparent to those skilled in the art that various modifications and variations can be made in the practice of the present invention without departing from the scope or spirit of the invention. One skilled in the art will recognize that the disclosed features may be used singularly, in any combination, or omitted based on the requirements and specifications of a given application or design. When an embodiment refers to "comprising" certain features, it is to be understood that the embodiments can alternatively "consist of" or "consist essentially of" any one or more of the features. Any of the methods disclosed herein can be used with any of the compositions disclosed herein or with any other compositions. Likewise, any of the disclosed compositions can be used with any of the methods disclosed herein or with any other methods. Other embodiments of the invention will be apparent to those skilled in the art from consideration of the specification and practice of the invention.

It is noted in particular that where a range of values is provided in this specification, each value between the upper and lower limits of that range is also specifically disclosed. The upper and lower limits of these smaller ranges may independently be included or excluded in the range as well. The singular forms "a," "an," and "the" include plural referents unless the context clearly dictates otherwise. It is intended that the specification and examples be considered as exemplary in nature and that variations that do not depart from the essence of the invention fall within the scope of the invention. Further, all of the references cited in this disclosure are each individually incorporated by reference herein in their entireties and as such are intended to provide an efficient way of supplementing the enabling disclosure of this invention as well as provide background detailing the level of ordinary skill in the art.

What is claimed is:

1. A method of treating insomnia in a patient with the insomnia, the method comprising:
    administering a pharmaceutical composition to a patient having insomnia;
        wherein the pharmaceutical composition comprises ebastine and alprazolam, and wherein the ebastine is present in the pharmaceutical composition from about 5 mg to about 50 mg, and wherein the alprazolam is present in the pharmaceutical composition from about 0.2 mg to about 2 mg.

2. The method of claim 1, wherein the pharmaceutical composition is administered once a day, or once every 2 or 3 or 4 days to the patient in an oral solid or liquid form.

3. The method of claim 1, wherein the pharmaceutical composition is administered twice a day.

4. The method of claim 1, wherein the pharmaceutical composition is administered once every 2 or 3 or 4 days.

5. The method of claim 1, wherein the pharmaceutical composition is administered in an oral solid form.

6. The method of claim 1, wherein the pharmaceutical composition is administered in a liquid form.

7. A method of treating insomnia in a patient with the insomnia, the method comprising:
    administering a pharmaceutical composition to a patient having insomnia;
        wherein the pharmaceutical composition comprises ebastine in an amount in the range of about 5 mg to about 25 mg and alprazolam in an amount in the range of about 0.2 mg to about 2 mg.

8. The method of claim 7, wherein the pharmaceutical composition is administered once a day, or once every 2 or 3 or 4 days to the patient in an oral, solid or liquid form.

9. The method of claim 7, wherein the pharmaceutical composition is administered twice a day.

10. The method of claim 7, wherein the pharmaceutical composition is administered once every 2 or 3 or 4 days.

11. The method of claim 7, wherein the pharmaceutical composition is administered in an oral solid form.

12. The method of claim 7, wherein the pharmaceutical composition is administered in a liquid form.

* * * * *